US009089299B2

(12) United States Patent
Nowak et al.

(10) Patent No.: US 9,089,299 B2
(45) Date of Patent: Jul. 28, 2015

(54) POSTERIOR LUMBAR RETRACTOR SYSTEM

(76) Inventors: Steve Nowak, Traverse City, MI (US); Christopher T. Martin, Empire, MI (US); Daniel K. Farley, Traverse City, MI (US); Stephanie Zalucha, Traverse City, MI (US); John Thalgott, Las Vegas, NV (US); Josh Delickta, Elk Rapids, MI (US)

( * ) Notice: Subject to any disclaimer, the term of this patent is extended or adjusted under 35 U.S.C. 154(b) by 429 days.

(21) Appl. No.: 13/415,543

(22) Filed: Mar. 8, 2012

(65) Prior Publication Data

US 2013/0030254 A1   Jan. 31, 2013

Related U.S. Application Data

(63) Continuation of application No. 12/959,701, filed on Dec. 3, 2010, now abandoned.

(60) Provisional application No. 61/266,373, filed on Dec. 3, 2009.

(51) Int. Cl.
  *A61B 1/32* (2006.01)
  *A61B 17/02* (2006.01)

(52) U.S. Cl.
  CPC ............... *A61B 1/32* (2013.01); *A61B 17/0206* (2013.01); *A61B 17/02* (2013.01)

(58) Field of Classification Search
  CPC ............................ A61B 17/0206; A61B 1/32
  USPC .......... 600/215, 219, 222, 224, 225, 228, 231
  See application file for complete search history.

(56) References Cited

U.S. PATENT DOCUMENTS

| 4,263,899 | A | * | 4/1981 | Burgin | 600/213 |
|---|---|---|---|---|---|
| 4,747,394 | A | * | 5/1988 | Watanabe | 600/232 |
| 4,989,587 | A | * | 2/1991 | Farley | 600/228 |
| 5,088,472 | A | * | 2/1992 | Fakhrai | 600/214 |
| 5,667,481 | A | * | 9/1997 | Villalta et al. | 600/224 |
| 5,944,658 | A | * | 8/1999 | Koros et al. | 600/232 |
| 6,033,363 | A | | 3/2000 | Farley et al. | |
| 6,511,423 | B2 | | 1/2003 | Farley | |
| 6,712,795 | B1 | * | 3/2004 | Cohen | 604/233 |

(Continued)

OTHER PUBLICATIONS

PCT, Notification of the Transmittal of the International Search Report and the Written Opinion of the International Searching Authority, or the Declaration, in International application No. PCT/US2010/058839, dated Feb. 7, 2011.

(Continued)

*Primary Examiner* — Ellen C Hammond
(74) *Attorney, Agent, or Firm* — McAndrews, Held & Malloy, Ltd.

(57) ABSTRACT

A retractor system includes a frame and first and second retractor blades. The frame includes first and second securement features. At least one of the first and second securement features is movable with respect to the frame when the first and second securement features is mounted to the frame. Proximal portions of the first and second refractor blades are secured proximate the first and second securement features respectively. In a first position the first and second refractor blades are laterally opposed. Movement of the securement feature adjusts the angle of at least one of the retractor blades so that at least one of the retractor blades may be adjusted between an acute angle and an obtuse angle to horizontal.

16 Claims, 7 Drawing Sheets

(56) References Cited

U.S. PATENT DOCUMENTS

| | | | |
|---|---|---|---|
| 6,746,467 B1 * | 6/2004 | Taylor et al. | 606/199 |
| 7,582,058 B1 | 9/2009 | Miles | |
| 8,062,218 B2 * | 11/2011 | Sebastian et al. | 600/229 |
| 8,211,012 B2 * | 7/2012 | Wing et al. | 600/215 |
| 2002/0077531 A1 | 6/2002 | Puchovsky | |
| 2004/0176665 A1 * | 9/2004 | Branch et al. | 600/210 |
| 2005/0070765 A1 | 3/2005 | Abdelgany | |
| 2007/0021656 A1 | 1/2007 | Martin | |
| 2008/0058606 A1 | 3/2008 | Miles | |
| 2009/0259107 A1 | 10/2009 | Crenshaw | |
| 2009/0275804 A1 | 11/2009 | Bertagnoli | |
| 2010/0217089 A1 | 8/2010 | Farley | |
| 2012/0136215 A1 | 5/2012 | Farley | |

OTHER PUBLICATIONS

PCT, Notification Concerning Transmittal of International Preliminary Report on Patentability (Chapeter I of the Patent Cooperation Treaty), in International application No. PCT/US2010/058839, dated Jun. 14, 2012.

Office action in U.S. Appl. No. 12/959,701, dated Sep. 18, 2012, (13 pages).

* cited by examiner

POSTERIOR LUMBAR RETRACTOR SYSTEM

CROSS-REFERENCE TO RELATED APPLICATION

The present application claims priority to U.S. application Ser. No. 12/959,701 having a filing date of Dec. 3, 2010, which claims priority to, and claims benefit of U.S. Provisional Application No. 61/266,373, filed Dec. 3, 2009, the complete subject matter of which is hereby incorporated by reference in its entirety.

STATEMENT REGARDING FEDERALLY SPONSORED RESEARCH OR DEVELOPMENT

None.

BACKGROUND OF THE INVENTION

The present invention relates to surgical apparatus for retracting anatomy to provide exposure of an operative site, and more particularly relates to retraction apparatus providing improved access to an operative site for a posterior lumbar procedure.

In surgical operations, retraction devices are used to properly access internal organs and bone structures. Retraction devices are generally designed to hold back the anatomy in the immediate area of the operative site to enable a surgeon to have both an optimal view of the site and a sufficiently-open area within which to work. During a surgical procedure, a surgeon will typically make an incision in a patient to access the sites of interest, such as an internal organ or organs, and/or bone structures, depending on the procedure. A retraction device may then be used to maintain clear access to the site of interest.

In many known retractor systems, retractor blades are rigidly attached to a frame at an angle, such as about 90 degrees from horizontal (i.e. generally vertical). Such a fixed angle limits the flexibility of the system to provide different shapes of access areas.

Ideally, such access would include room to manipulate the various surgical implements required, as well as good lighting and visibility. Further, it may be desirable for such access to allow for adjustability to accommodate different patients or procedures.

It is therefore one object of the present invention to provide a surgical retractor that provides improved access, and/or visibility, and/or adjustability, and/or maneuverability around a surgical site of interest.

BRIEF SUMMARY OF THE INVENTION

These and other objects of the invention are achieved in a retractor system. In one embodiment of the present invention, a retractor system includes a frame and first and second retractor blades. The frame includes first and second securement features. At least one of the first and second securement features is movable with respect to the frame when the at least one of the first and second securement features is mounted to the frame. The first and second retractor blades each have a distal portion and a proximal portion. The proximal portions of the first and second retractor blades are configured to be secured proximate to the first and second securement features respectively, such that the first and second retractor blades may be positioned in a first position wherein the first and second retractor blades are laterally opposed. A movement of the at least one securement feature that is movable with respect to the frame adjusts the angle of at least one of the retractor blades, wherein the at least one of the retractor blades may be adjusted between a first angle less than 90 degrees to horizontal and second angle greater than 90 degrees to horizontal.

In certain embodiments, the distal portions of the first and second retractor blades are securable to a portion of a patient's anatomy during a surgical procedure. The at least one securement feature that is movable with respect to the frame is configured to move the proximal portion of at least one of the retractor blades while the distal portions of the retractor blades remain secured proximal to an operative site. Further, in certain embodiments, the at least one securement feature that is configured to move with respect to the frame is configured to adjust the angular position of at least one of the retractor blades when the at least one securement feature is moved in a substantially lateral direction.

In certain embodiments, the at least one securement feature that is configured to move with respect to the frame is configured so that the angular and lateral position of the retractor blade secured to the at least one securement feature are independently adjustable.

In certain embodiments, the first securement feature includes a fixed arm that is fixed relative to the frame, and the second securement feature includes a movable arm that is movable with respect to the frame. Further, in certain embodiments, the frame includes a spreader bar that extends between the first and second securement features. The spreader bar includes teeth that form a rack, and the second securement feature includes a pinion that cooperates with the rack to facilitate lateral movement of the movable arm with respect to the fixed arm.

In certain embodiments, the first and second securement features include first and second anus, respectively, that are joined by a pivot.

In one embodiment of the present invention, a retractor system includes a spreader bar, a first positioning assembly, and a second positioning assembly. The first positioning assembly is adapted to secure a first retractor blade and is movably secured to the spreader bar. The first positioning assembly includes a first lateral positioning assembly for moving the first positioning assembly laterally along at least a first portion of a length of the spreader bar. The first positioning assembly also includes a first angular positioning assembly for adjusting an angle of the first retractor blade relative to the spreader bar. The second positioning assembly is adapted to secure a second retractor blade. The second positioning assembly is movably secured to the spreader bar, and includes a second lateral positioning assembly for moving the second positioning assembly laterally along at least a second portion of the length of the spreader bar. Also, the second positioning assembly includes a second angular positioning assembly for adjusting an angle of the second retractor blade relative to the spreader bar. The first and second positioning assemblies are de-coupled wherein the first and second retractor blades may be moved independently of each other.

In certain embodiments, the first lateral positioning assembly and first angular positioning assembly are de-coupled wherein the angle and lateral position of the first retractor blade are independently adjustable.

In certain embodiments, the spreader bar includes teeth that form a rack. The first and second lateral positioning assemblies each include a pinion that cooperates with the rack to facilitate lateral movement of the first and second positioning assemblies with respect to each other. The first and second lateral positioning assemblies may further each include a locking lever that cooperates with the teeth to secure in place the positioning assembly with which the locking lever is associated.

In certain embodiments, the first and second angular positioning assemblies include a threaded post and an arm. The arm includes features that threadedly accept the threaded post, wherein rotation of the threaded post changes the angle of the arm. In certain embodiments, the first and second positioning assemblies each include a body and an arm. The body accepts the arm, and the arm is configured to accept a portion of the retractor blade associated with the positioning assembly.

In certain embodiments, the first lateral positioning assembly, first angular positioning assembly, second lateral positioning assembly, and second angular positioning assembly are configured to be independently adjustable by a substantially similarly sized tool.

DETAILED DESCRIPTION

Figure 1:
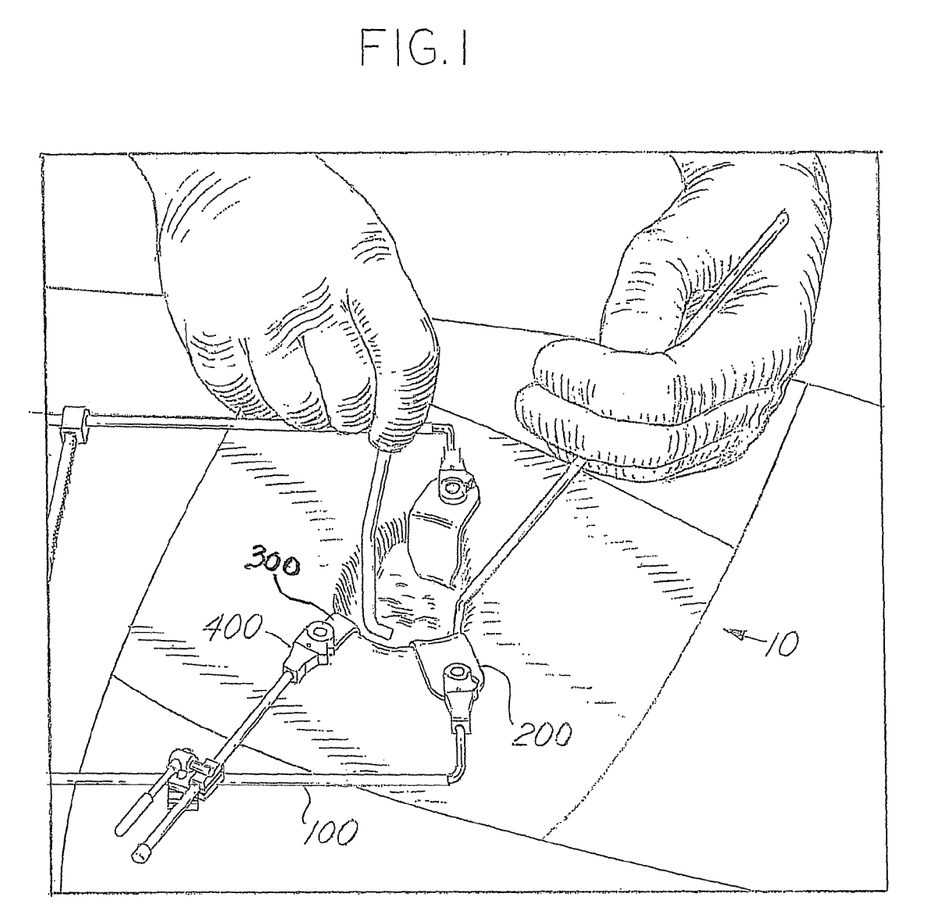
FIG. 1 provides a perspective view of a posterior lumbar retractor system formed in accordance with an embodiment of the present invention.

FIG. 1 illustrates an embodiment of a posterior retractor system 10 formed in accordance with an embodiment of the present invention. In the illustrated embodiment, the retractor system 10 includes a blade spreader frame 100, a plurality of retractor blades 200, 300, and an adjustment arm 400. The various components of the retractor system 10 may be made, for example, of stainless steel. While an embodiment particularly well adapted for posterior lumbar surgery is discussed below and illustrated in the figures, the disclosed technology is not so limited and may be used for other procedures as well.

Figure 2:
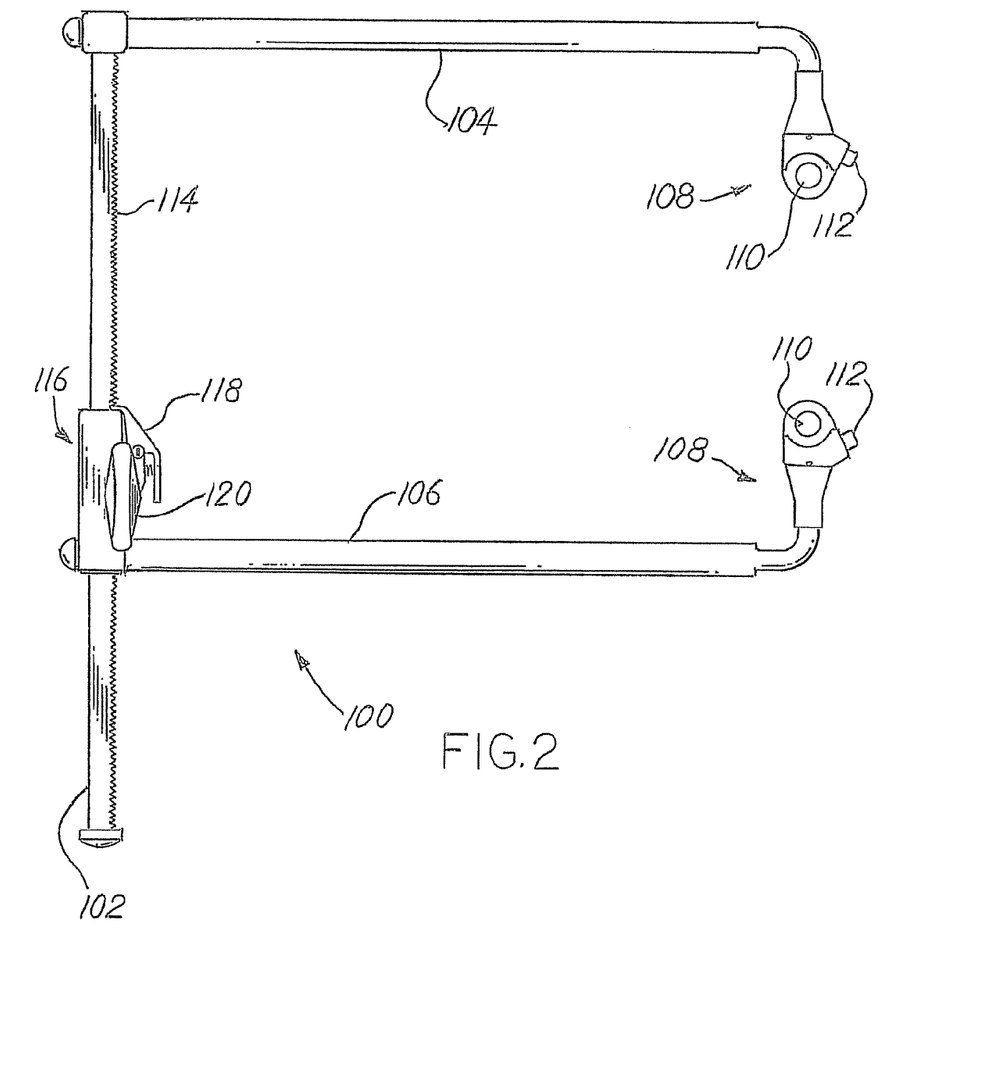
FIG. 2 provides a top view of a blade spreader formed in accordance with an embodiment of the present invention.

FIG. 2 illustrates an embodiment of a blade spreader frame 100 formed in accordance with an embodiment of the present invention. The blade spreader frame 100 includes a spreader bar 102, a first arm 104, and a second arm 106. The blade spreader frame 100 may be similar in certain regards to the blade spreader described in U.S. patent application Ser. No. 12/433,226, titled "Hinged Retractor with Sheath," filed Apr. 30, 2009, which is hereby incorporated by reference in its entirety.

The illustrated retractor system 10 is an example of a retractor system that includes a fixed arm and a movable arm that each hold a retractor. In the illustrated embodiment, the first arm 104 is fixed toward one end of the spreader bar 102, and extends generally perpendicularly from the spreader bar 102. The first arm 104 includes a blade securement assembly 108 positioned proximate to the end of the first arm 104 farthest away from the spreader bar 102. The blade securement assembly 108 is configured to accept and secure a retractor blade to the first arm 104. The first arm 104 of the illustrated embodiment includes an opening 110, a securement mechanism 112, and an internal ball (not shown). The securement mechanism 112 is configured to secure the ball in a fixed position, and to allow the ball to be released from a fixed position. For example, the illustrated securement mechanism 112 is a button. When the button is pushed, the ball is released from a constrained position and has some freedom of movement relative to the opening 110. When the button is released, the ball is constrained such that it extends into the opening 110. In this way, the securement mechanism 108 may cooperate with a groove on a mounting feature of a retractor blade to secure the blade in place while allowing the blade to pivot relative to the securement mechanism 108. For example, with the button depressed and the ball free to move, a mounting feature of a retractor blade may be introduced into the opening 110. With the retractor in place, the button, is released, constraining the ball, which now extends into the opening and is accepted by a groove in the mounting feature of the retractor blade, which prevents the retractor blade from being removed from the opening 110. To release the blade, the button is depressed.

The second arm 106 is movable along at least a portion of the length of the spreader bar 102. In the illustrated embodiment, the spreader bar 102 includes teeth 114 that cooperate with an adjustment assembly 116 to position the second arm 106 along the length of the spreader bar 102. For example, the illustrated adjustment assembly includes an arm lock 118 and a thumbwheel 120. The thumbwheel 120 actuates a gear (not shown) that cooperates with the teeth 114 to form a rack and pinion. When the thumbwheel 120 is turned, the second arm 106 thus moves along the length of the spreader bar 102. The arm lock 118 of the illustrated embodiment functions as a ratcheting mechanism. The arm lock 118 rotates about a pivot, and is urged by a spring (not shown) into place against the teeth 114. The arm lock 118 is sized and configured to pivot against that spring when the second arm 106 is urged in one direction (for example, in a direction that moves the second arm 106 away from the first arm 104), but not pivot against the spring when the second arm 106 is urged in the opposite direction. Thus, the second arm 106 can be moved away from the first arm 104 by turning the thumbwheel 120, but the bars will be secured in an open position during a procedure. To move the anus together, the lock 118 may be manually pivoted against the spring using a thumb lever, and the thumbwheel 120 turned in the desired direction. In alternate embodiment, different mechanisms may be used to move and/or position the second arm 106 along the length of the spreader bar 102. In further alternate embodiments, the blade spreader frame may be fixed to a frame and/or be oriented for different arrangements of movable arms, such as, for example, as illustrated and described in the application Ser. No. 12/433,226 referenced above.

The second arm 106 includes a blade securement mechanism 108 similar to that described above. Further, in the illustrated embodiment, the first arm 104 and second arm 106 are configured to accept adjustment arms (described below) along at least a portion of their length. For example, the arms 104, 106 are substantially cylindrical along their lengths and sized to accept a clamp of an adjustment arm.

Figure 3:
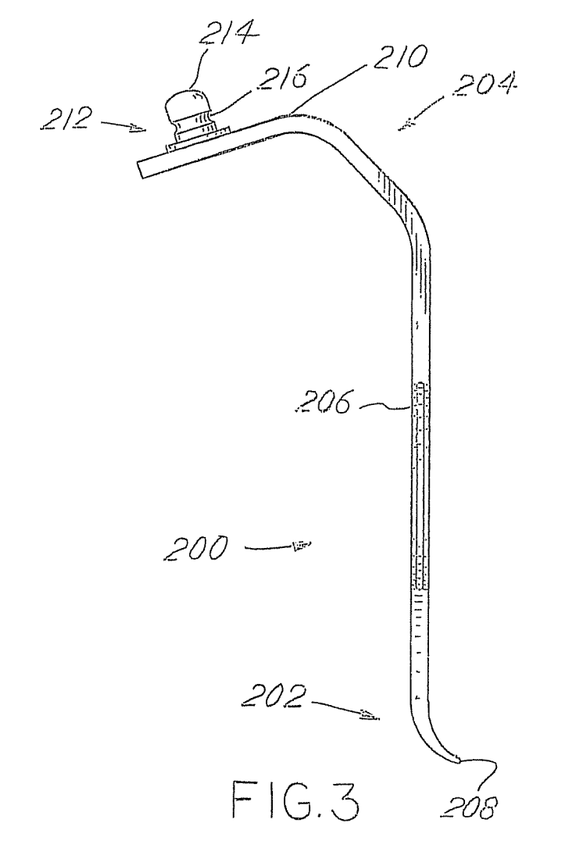
FIG. 3 illustrates a side view of a retractor blade formed in accordance with an embodiment of the present invention.
Figure 4:
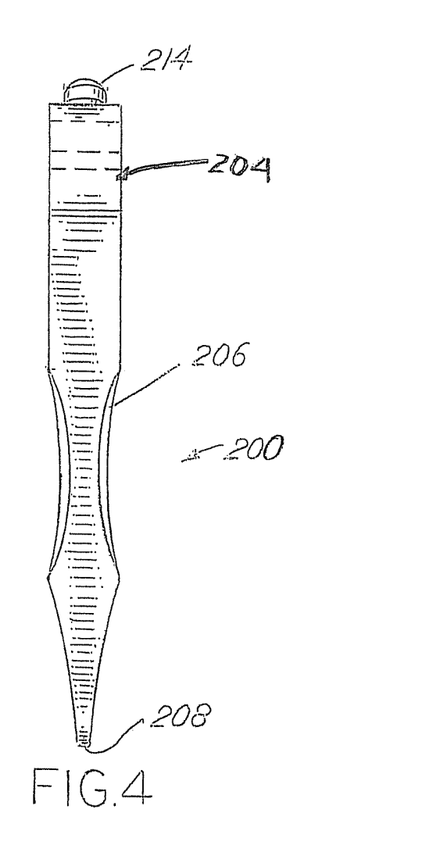
FIG. 4 illustrates a front view of the retractor blade of FIG. 3.

FIG. 3 illustrates a side view of a first retractor blade 200 formed in accordance with an embodiment of the present invention, and FIG. 4 illustrates a front view of the first retractor blade 200. The first retractor blade 200 includes a distal end 202, a proximal end 204, a body 206, an engagement tip 208, a handle 210, and a mounting feature 212. The distal end 202 is the end of the first retractor blade 200 that is oriented inside of the patient during a procedure, with the proximal end 204 oriented closer to the practitioner with the blade in place during a procedure.

The first retractor blade 200 includes a body 206. Various overall lengths of the body may be used depending on the particular patient and/or procedure. For example, the overall length of the body may be, for example, about 80 millimeters, about 100 millimeters, or about 120 millimeters. Similarly, retractors having various widths may be used depending on the particular patient and/or procedure. The body is shaped to allow access to a surgical site of interest while also limiting the amount of tissue that has to be retracted to limit trauma that may occur to such tissue during a procedure. In the illustrated embodiment, for example, the sides of the body 206 have areas of reduced width and thickness as illustrated. Further, the width of the body 206 tapers distally toward a tip as illustrated. In the illustrated embodiment, the body 206 may have an overall width of about 14 millimeters. The retractor system 10 may include a variety of shapes, lengths, and widths of retractor blades.

Proximate to the distal end 202, the first retractor blade 200 includes an engagement tip 208. In the illustrated embodiment, the engagement tip 208 is a point configured to be temporarily insertable into a feature of the patient's anatomy and secured during a procedure without doing undue damage to the feature into which it is inserted, and removable after the procedure. In alternate embodiments, other means of fixing the distal end 202 may be used.

The handle 210 is located proximate to the proximal end 204. The handle 210 is sized, shaped, and configured to provide a surface for a practitioner to hold and utilize to manipulate and position the first retractor blade 200 during a procedure.

Extending from the handle 210 is a mounting feature 212. The mounting feature 212 is used to secure the retractor blade to the first arm 104, second arm 106, or an adjustment arm 400. In the illustrated embodiment, the mounting feature 212 is sized and configured to cooperate with a mechanism on the bars or adjustment arm to position and/or releasably secure the first retractor blade 200 in place during a procedure. The mounting feature 212 illustrated in FIG. 3 includes a nipple 214 and a groove 216 configured to cooperate with an opening of blade securement mechanism of first arm 104, second arm 106, or an adjustment arm 400. For example, when securing a first retractor blade 200 to the first arm 104, the mounting feature 212 is accepted by the opening 110, and may be secured in place by the cooperation of the groove 216 of the first retractor blade 200 and the ball of the blade securement mechanism 108 of the first arm 104.

Figure 5:
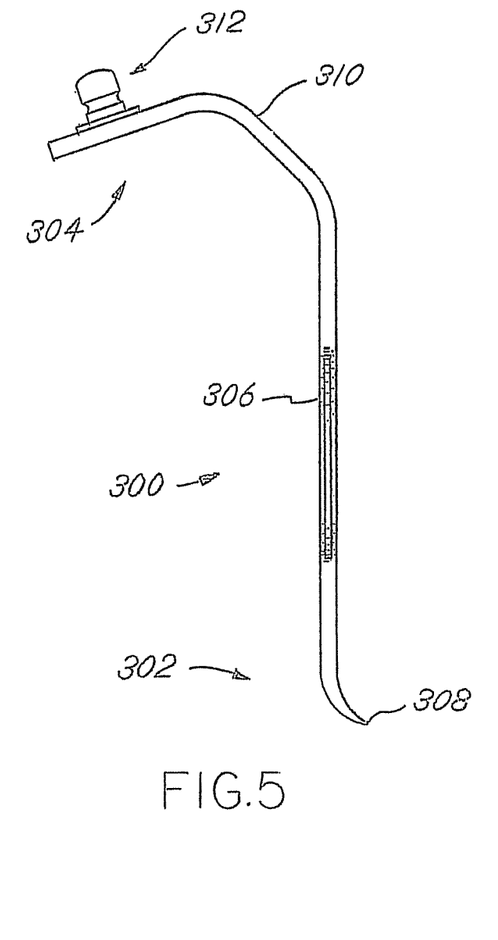
FIG. 5 illustrates a side view of a retractor blade formed in accordance with an embodiment of the present invention.
Figure 6:
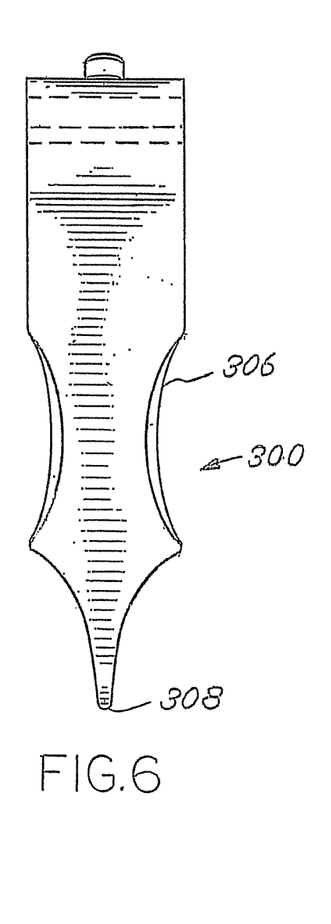
FIG. 6 illustrates a front view of the retractor blade of FIG. 5.

FIGS. 5 and 6 illustrate a second retractor blade 300 that is generally similar in many respects to first retractor blade 200, but is wider. The second retractor blade 300 includes a distal end 302, a proximal end 304, a body 306, an engagement tip 308, a handle 310, and a mounting feature 312. For example, the overall length of the body 306 may be, for example, about 80 millimeters, about 100 millimeters, or about 120 millimeters. In the illustrated embodiment, the overall width is about 28 millimeters.

Figure 7:
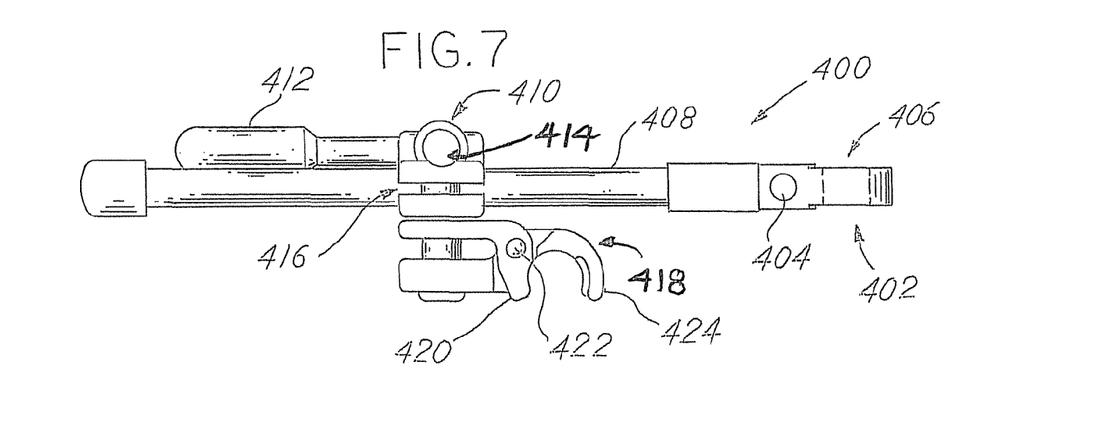
FIG. 7 illustrates a top view of an adjustment arm formed in accordance with an embodiment of the present invention.

FIG. 7 illustrates a top view of an adjustment arm 400 formed in accordance with an embodiment of the present invention. The adjustment arm 400 includes a blade securement assembly 402, a body 408, and a mounting mechanism 410. The adjustment 400 provides an adjustable means of securing additional retractor blades to the blade spreader frame 100.

The blade securement assembly 402 includes an opening 406, a securement mechanism 404, and a ball (not shown). The blade securement assembly 402 may be arranged substantially similarly to the blade securement assembly described above. As one example of a potential difference, the opening 406 may not be entirely circular, but instead be defined by a truncated arc. The blade securement assembly 402 cooperates with a mounting feature of a retractor blade to engage the retractor blade to the adjustment arm 400.

The mounting mechanism 410 of the illustrated embodiment is configured to be movable along at least a portion of the length of the body 408, and includes a handle 412, an actuating mechanism 414, a body securing mechanism 416, and a bar securing mechanism 418. In the illustrated embodiment, the actuating mechanism 414 is a cam, and the body securing mechanism 416 and bar securing mechanism 418 include jaws that are opened and closed by the movement of the cam. For example, when the handle 412 is moved from an open position into a locked position by rotation in the clockwise direction as seen in FIG. 7, the rotation of the cam acts to close the jaws 416 around the body 408, securing the mounting mechanism in place along the length of the body. At the same time, the rotation of the cam urges against the lever arm of a movable jaw 420 about a pivot 422, wherein the movable jaw 420 and fixed jaw 424 cooperate to securably grasp the body of one of the first and second support bars 102, 104, thus securing the adjustment arm 400 along the length of the support bar to which it is mounted. The movable jaw 420 and the fixed jaw 424 are sized and configured so that they may be clipped onto the first arm 104 or second arm 106 with the handle 412 in an open position, and so that the adjustment arm 400 is secured in place to the support bar with the handle 412 in a closed position.

Figure 8:
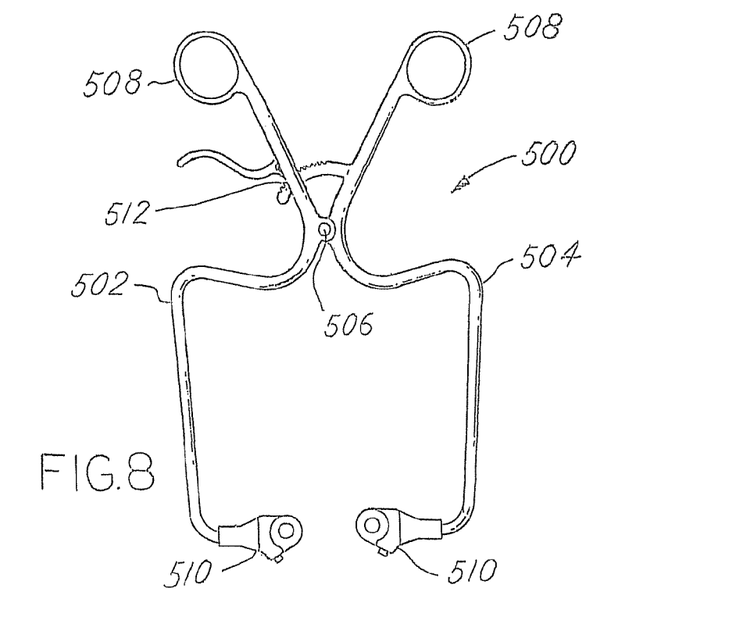
FIG. 8 illustrates an embodiment of a hand held frame formed in accordance with an embodiment of the present invention.

In alternate embodiments, only two retractors may be necessary. FIG. 8 illustrates a handheld frame 500 formed in an accordance with an embodiment of the present invention that may be used in such procedures. The illustrated handheld frame 500 provides one example of a system that includes two arms that are linked, with each arm holding a retractor. The handheld frame 500 includes a first arm 502, a second arm 504, a pivot 506, handles 508, blade securement assemblies 510, and a locking mechanism 512. The first and second arms 502, 504 each include a handle 508 and a blade securement assembly 510. The handles 508 are sized and configured to provide convenient grasping and actuating of the handheld frame 500 by a practitioner. The blade securement assemblies are used to secure retractor blades to the handheld frame 500, and may be substantially as described above. The first and second arms 502, 504 are joined about the pivot 506, such that urging the handles 508 together moves the blade securement assemblies 510 apart. The locking mechanism 512 is configured to secure the position of the first and second arms 502, 504 in a desired position during a procedure. For example, the locking mechanism may include a rotatable arm that engages teeth. In certain embodiments, the handheld frame 500 may also be fixed in place and, for example, secured to a frame that attaches to a hospital bed.

Following is a general overview of how certain embodiments of a retractor system formed in accordance with the present invention may be used during a procedure where access is required to spinous processes. First an incision is made over the processes to which access is desired. Next, an appropriately sized retractor blade, such as second retractor blade 300, is selected and inserted into the incision, such that the engagement tip of the retractor blade engages the lateral aspect of the facet joint capsule of the patient, and the blade is retracted manually. An additional retractor blade is next inserted to engage the lateral aspect of the opposite facet joint and retracted manually.

If only a single level exposure (i.e. access to one disc) is desired, there may only be the need for only two retractor blades. The handheld frame 500 may be utilized for such a procedure requiring only two retractor blades. The mounting features of the retractor blades are secured to the blade securement assemblies of the handheld frame, and the handles of the handheld frame 500 are brought together to distract the retractor blades until the desired exposure is achieved.

Other procedures may require a larger access area. A frame such as blade spreader frame 100 may be used, for example, if multi level exposure requires the use of more retractor blades. In an embodiment formed in accordance with the present invention, after two retractor blades are engaged as described above, one retractor blade is secured to the first arm 104 and the other retractor blade is secured to the second arm 106. The thumbwheel is then turned to retract the blades to a desired position. Additional retractor blades, such as first retractor blades 200, may then be added. To add an additional retractor blade, the retractor blade is inserted into the incision and engaged with a feature of the patient's anatomy. An adjustment arm 400 is then clipped on to an appropriate location along one of the first or second bars. The retractor blade is then secured to the adjustment arm and positioned as desired. Once the desired position is achieved, the handle of the adjustment arm is moved to the locked position, securing the retractor blade in its desired position. Additional retractor blades may then be added, positioned, and secured in a similar fashion, as necessary.

Thus, the above described embodiments provide beneficial exposure and control of exposure to surgical sites of interest, allowing good visibility and access, for example, for treating segmental dysfunctions, spinal stenosis, and disc herniations. Further, the narrow blade tips help provide clear access while avoiding and/or reducing the interruption of screw trajectory for procedures that require the placement of screws. The various mechanisms described for positioning retractors allows for quick, easy addition of independent retractors, improving versatility and flexibility in providing access. Additionally, the handheld frame allows for simple operation of single level procedures. Further still, the use of the above described retractor system allows for retractor blades to be levered off of, for example, the spine at various angles. For example, an angle of greater than 90 degrees (creating, in effect, a funnel shape) may provide increased exposure at the surface of the incision relative to the volume inside a patient. Or, alternatively, an angle of less than 90 degrees (creating, in effect, an upside down funnel shape) may be utilized if less exposure is required, and/or to create a larger volume of working area inside the patient relative to the incision size, to reduce potential damage to muscle tissue being retracted.

Figure 9:
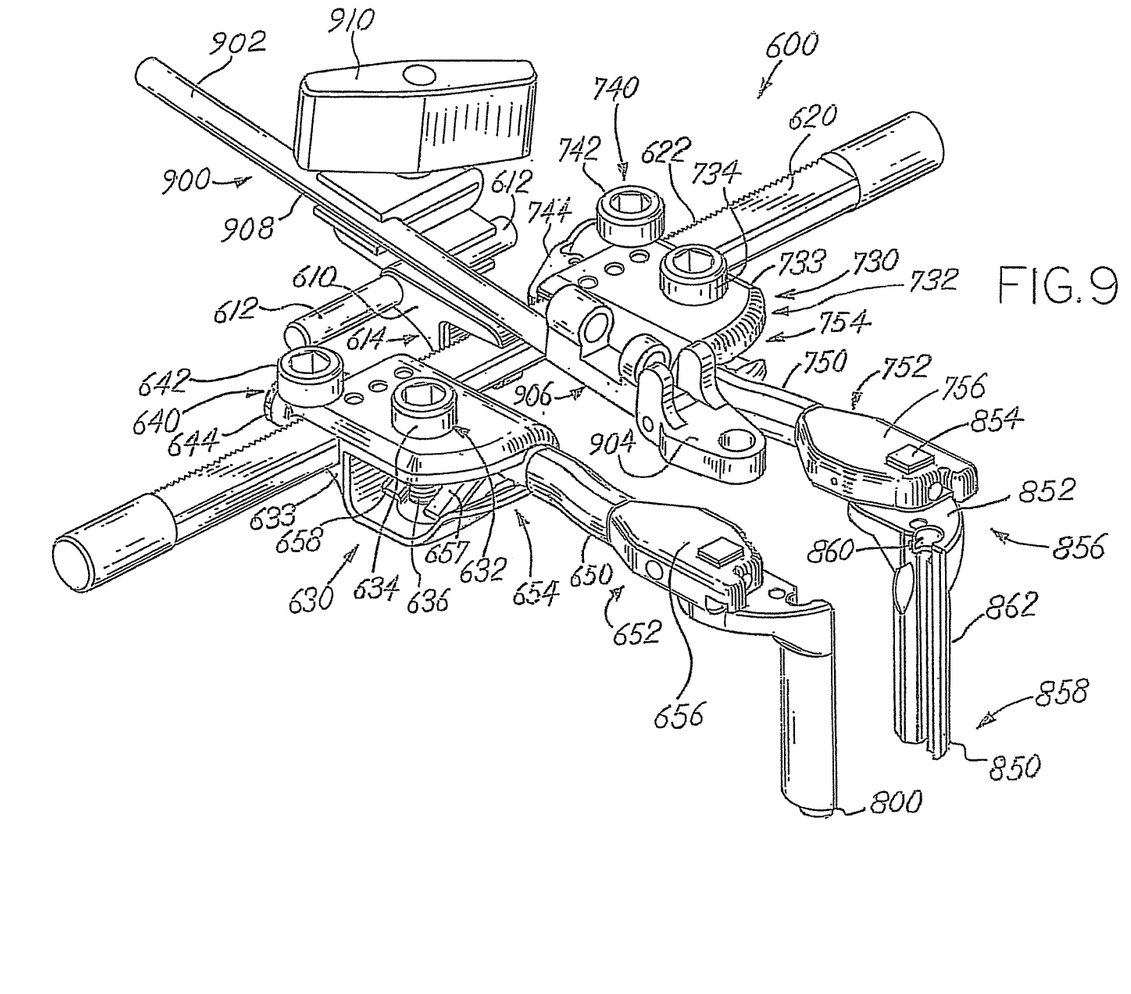
FIG. 9 illustrates a perspective view of a posterior lumbar retractor system formed in accordance with an embodiment of the present invention.

Other arrangements of retractors are also contemplated. For example, FIG. 9 illustrates a perspective view of a posterior lumbar retractor system 600 formed in accordance with an embodiment of the present invention. The illustrated posterior lumbar retractor system 600 provides an example of a retractor system having two arms that hold retractors that are independently movable. The posterior lumbar retractor system includes a mounting member 610, a spreader bar 620, a first positioning assembly 630, a second positioning assembly 730, a first retractor 800, a second retractor 850, and an auxiliary retractor assembly 900. The first retractor 800 and second retractor 850 mount to the first positioning assembly 630 and second positioning assembly 730, respectively. The first positioning assembly 630 and the second positioning assembly 730 mount independently to the spreader bar 620, and are examples of movable securement features that can adjust the proximal and/or distal portions of retractor blades which may not be secured at their distal ends. Further, the spreader bar 620 is mounted via the mounting member 610 to an external frame (not shown) that may be secured in turn, for example, to a hospital bed. The auxiliary retractor assembly 900 also mounts to the mounting member 610.

The mounting member 610 is used to mount the spreader bar 620 and/or other components to an external frame that may be attached, for example, to a hospital bed. In the illustrated embodiment, the mounting member 610 includes bars 612 and jaws 614. The bars 612 extend horizontally to either side of the center of the mounting member 610, and provide a convenient location for securing clamps that may be used to secure components to the mounting member 610, and/or to secure the mounting member 610 to a frame. The jaws 614 define an opening that is sized to accept the spreader bar 620 so that the spreader bar 620 may be secured to the mounting member 610. For example, the jaws 614 may include an upper and lower prong that are resiliently biasable to accept the spreader bar 620 and use a spring-like action to hold the spreader bar 620 in place. As another example, the jaws 614 may include an actuating mechanism, such as a threaded member, that may be used to draw upper and lower prongs of the jaws 614 together to hold the spreader bar 620 in place, and draw apart the prongs of the jaws 614 to release the spreader bar 620. In certain embodiments, other types of mounting members or clamps may be used to secure the spreader bar 620 to a frame.

In the illustrated embodiment, the spreader bar 620 is a generally straight bar. The spreader bar includes teeth 622 that form a rack that accepts a pinion allowing the first positioning assembly 630 and second positioning assembly 730 to be adjusted laterally along the length of the spreader bar 620. The length of the spreader bar 620 is sized to provide for movement and adjustability of the first positioning assembly 630 and second positioning assembly 730. The cross section of the spreader bar 620 is configured so that at least a portion of the spreader bar 620 may be accepted by the jaws 614 of the mounting member 610.

In the embodiment illustrated, the first positioning assembly 630 and the second positioning assembly 730 are similar in many respects but are formed as mirror images of each other. In certain embodiments, the first and second positioning assemblies may be similar or identical, and in certain embodiments, the first and second positioning assemblies may be more different. In the illustrated embodiment, the first positioning assembly 630 and the second positioning assembly 730 are laterally opposed such that a retractor held by each positioning assembly substantially faces a retractor held by the other positioning assembly when the retractors are generally parallel to each other and generally transverse to the spreader bar 620. Put another way, the inner surfaces of the retractors are oriented toward each other. Further, the positioning assemblies are adapted to allow both lateral and angular adjustment of the retractors. For example, the distal ends of the retractors may be angled away from each other, or they may be angled toward each other. Further still, in the illustrated embodiments, the movements of the retractor blades are not coupled to each other. Instead, the movements of the retractor blades are de-coupled, with the lateral and angular adjustments able to be performed independently of each other, and each retractor may be moved independently of the other.

The first positioning assembly 630 includes an angular positioning assembly 632, a body 633, a lateral positioning assembly 640, and an arm 650. The body 633 is movably mounted to the spreader bar 620 and accepts the arm 650. The angular positioning system 632 is adapted to adjust the angle at which an associated retractor is oriented into an incision. The lateral positioning assembly 640 is adapted to adjust the lateral positioning of an associated retractor relative to a patient, incision, and/or other retractor. The arm 650 is adapted to secure a retractor blade.

The angular positioning assembly 632 includes an angular adjustment member 634 and a grooved post 636. In the illustrated embodiment, the angular adjustment member 634 is formed similar to a bolt head and includes an opening for accepting a hex or allen key which can be used to rotate the angular adjustment member 634. Other mechanisms may be used as angular adjustment members. For example, the adjustment member could include a thumbwheel, tab, or winding mechanism for rotating by hand, or, as another example, a slotted or otherwise formed head. The grooved post 636 is accepted by the body 633 and rotates with the angular adjustment member 634. In the illustrated embodiment, the grooved post 636 includes threads that cooperate with a feature or features on the arm 650 to adjust the angle of the arm 650 when the grooved post 636 rotates. In the illustrated embodiment, a rotational movement is utilized to adjust the angle of the retractor. In certain embodiments, other mechanisms and/or movements may be utilized. Further still, mechanisms including, for example, a spring, or, as another example, a ratchet, may be utilized to help lock a retractor in place and/or help bias a retractor toward a default setting.

The body 633 is configured to accept and secure the arm 650. The body 633 also is configured to accept the lateral positioning assembly 640 and the angular positioning assembly 632. The body 633 is also configured to be mounted to the spreader bar 620 such that the lateral positioning assembly 640 may be used to move the body 633 along at least a portion of the length of the spreader bar 620.

The lateral positioning assembly 640 includes a lateral adjustment member 642 and a lock 644. In the illustrated embodiment, the lateral adjustment member 642 is associated with a gear or pinion (not shown) that cooperates with the teeth 622 to move the first positioning assembly 630 laterally along a portion of the length of the spreader bar 622 when the lateral positioning member 642 is rotated. In the illustrated embodiment, the lateral adjustment member 642 is formed similar to a bolt head and includes an opening for accepting an allen key which can be used to rotate the lateral adjustment member 642. Other mechanisms may be used as angular adjustment members. For example, the adjustment member could include a thumbwheel, tab, or winding mechanism for rotating by hand, or, as another example, a slotted head. For convenience, the lateral adjustment member 642 may accept an adjustment tool, such as, for example, an allen key, that is compatible with the angular adjustment member 634. In the illustrated embodiment, the lock 644 includes a handle and a portion that engages the teeth 622 of the spreader bar 620. Depressing the handle of the lock 644 disengages the lock from the teeth 622, and allowing the first positioning assembly 630 to move along the length of the spreader bar 620. In certain embodiments, the lock includes a ratcheting mechanism that permits movement in one direction (for example, the direction away from the center of the incision) but resists movement in the other direction.

The arm 650 includes a first portion 652 and a second portion 654. The first portion 652 is oriented toward a retractor blade and includes a head 656. The head 656 is adapted to accept and secure a retractor blade. For example, the head 656 may include an opening that accepts a post of a retractor blade. The second portion 654 is oriented toward the body 633 and includes a first arm 657 and a second arm 658. In the illustrated embodiments, the first arm 657 and second arm 658 are spaced apart to accept the grooved post 636, and are configured (for example, by including corresponding grooves) so that rotation of the grooved post urges the first arm 657 and second arm 658 upward or downward. Rotation of the grooved post 636 in a first direction urges the first and second arms 657, 658 upward, thereby rotating the arm (and associated retractor blade) in a first direction, while rotation of the grooved post 636 in the opposite direction urges the first and second arms 657, 658 downward, thereby rotating the arm 650 (and associated retractor blade) in the opposite direction. In the illustrated embodiment, the proximal end of the retractor blade is generally substantially aligned with an axis formed by the portion of the arm accepted and held by the body, so that rotation of the arm while it is held in the body results in little or no movement of the proximal end of the retractor blade, and more significant movement of the distal end of the retractor blade. The positioning of the first arm 657 and second arm 658 may be configured to provide a mechanical stop at either or both ends of a range of angles. Further, the pitch of the thread may be selected to adjust the fineness of the adjustability of the angle.

As mentioned above, the second positioning assembly 730 may be similar in many respects to the first positioning assembly 630 and include similar components. In the illustrated embodiment, the components of the second positioning assembly 730 generally correspond to the components of the first positioning assembly. For example, the second positioning assembly 730 includes an angular positioning assembly 732, a body 733, a lateral positioning assembly 740, and an arm 750. The body 733 is movably mounted to the spreader bar 620 and accepts the arm 750. The angular positioning system 732 is adapted to adjust the angle at which an associated retractor is oriented into an incision. The lateral positioning assembly 740 is adapted to adjust the lateral positioning of an associated retractor relative to a patient, incision, and/or other retractor. The arm 750 is adapted to secure a retractor blade.

Also generally similar to the first positioning assembly 630, the angular positioning assembly 732 includes an angular adjustment member 634 and a grooved post (not shown). In the illustrated embodiment, the angular adjustment member 734 is formed similar to a bolt head and includes an opening for accepting a hex or allen key which can be used to rotate the angular adjustment member 734. Again, other mechanisms may be used as angular adjustment members. For example, the adjustment member could include a thumbwheel, tab, or winding mechanism for rotating by hand, or, as another example, a slotted or otherwise formed head. The grooved post is accepted by the body 733 and rotates with the angular adjustment member 734. The grooved post may include threads that cooperate with a feature or features on the arm 750 to adjust the angle of the arm 750 when the grooved post rotates.

The body 733 is configured to accept and secure the arm 750. The body 733 also is configured to accept the lateral positioning assembly 740 and the angular positioning assembly 732. The body 733 is also configured to be mounted to the spreader bar 620 such that the lateral positioning assembly 740 may be used to move the body 733 along at least a portion of the length of the spreader bar 620.

Further generally similar to the first positioning assembly 630, the lateral positioning assembly 740 includes a lateral adjustment member 742 and a lock 744. In the illustrated embodiment, the lateral adjustment member 742 is associated with a gear or pinion (not shown) that cooperates with the teeth 622 to move the second positioning assembly 730 laterally along a portion of the length of the spreader bar 620 when the lateral positioning member 742 is rotated. In the illustrated embodiment, the lateral adjustment member 742 is formed similar to a bolt head and includes an opening for accepting an allen key which can be used to rotate the lateral adjustment member 642. Other mechanisms may be used as angular adjustment members. In the illustrated embodiment, the lock 744 includes a handle and a portion that engages the teeth 622 of the spreader bar 620. Depressing the handle of the lock 744 disengages the lock from the teeth 622, and allowing the second positioning assembly 730 to move along the length of the spreader bar 620. In certain embodiments, the lock includes a ratcheting mechanism that permits movement in one direction (for example, the direction away from the center of the incision) but resists movement in the other direction.

Similar to the arm 650, the arm 750 includes a first portion 752 and a second portion 754, with the first portion 752 oriented toward a retractor blade and including a head 756. The head 756 is adapted to accept and secure a retractor blade. The second portion 754 is oriented toward the body 733 and includes a first and second arm (not shown) that generally correspond to the first and second arms of the second portion 654 of the arm 650. In the illustrated embodiment, the proximal end of the retractor blade is generally substantially aligned with an axis formed by the portion of the arm accepted and held by the body, so that rotation of the while it is held in the body results in little or no movement of the proximal end of the retractor blade, and more significant movement of the distal end of the retractor blade.

The posterior lumbar retractor system 600 also includes a first retractor 800 and a second retractor 850 that are configured to mount to the first arm 650 and second arm 750, respectively. In the illustrated embodiment, the first retractor 800 and second retractor 850 are arranged so that their interior surfaces face the other retractor, or, put another way, they are laterally opposed. In the illustrated embodiment, the first retractor 800 and second retractor 850 are generally similar, but are mirror images of each other. As such, only the second retractor 850 will be described in greater detail below. In certain embodiments the first and second retractors may be identical, and in other embodiments the first and retractors may be more substantially different.

The second retractor 850 includes a proximal end 856 and a distal end 858. The proximal end 856 is oriented toward a practitioner when the second retractor 850 is in place in a patient, and the distal end 858 is oriented into the patient when the second retractor 850 is in place in a patient. The second retractor 850 includes a handle portion 852, a groove 860, and a retracting portion 862. The handle portion 852 is located proximate to the proximal end 856, and includes a post 854 extending therefrom that is accepted by the head 756 of the arm 750 of the second positioning assembly 730. In the illustrated embodiment, the groove 860 is formed by a bend or curve on an inner face of the second retractor 850 and may, for example, allow for placement of the second retractor 850 over a dilator, and/or, as another example, may facilitate placement of a screw or pin to secure the distal end 858 of the second retractor 850 to a portion of a patient's anatomy during a procedure. The retracting portion 862 is adapted to contact and hold back portions of a patient's anatomy during a procedure.

In the embodiment illustrated in FIG. 9, the posterior lumbar retractor system 600 also includes an auxiliary retractor assembly 900. The auxiliary retractor assembly 900 includes a bar 902 and a clamp 910. The clamp 910 secures the bar 902 to the mounting member 610. In certain embodiments, the clamp may join the bar to a spreader bar, for example, or, as another example, to a separate frame. The auxiliary retractor assembly 900 is configured to accept, position, and secure an auxiliary retractor (not shown). For example, a retractor assembly similar to those depicted in U.S. patent application Ser. No. 12/391,917, U.S. Publication No. 2010-0217089, which is hereby incorporated by reference in its entirety, may be used. In certain embodiments, there may be no auxiliary retractors. In certain embodiments, there may be more than one auxiliary retractor. Certain embodiments may use differently arranged clamp and/or arms to secure additional retractor blades.

In the embodiment illustrated in FIG. 9, the auxiliary retractor assembly 900 includes a bar 902, head 904 and adjustment housing 906. The bar 902 is configured to be accepted to the clamp 910 and may be joined to the head 904 by, for example, a pivot. The head 904 is configured to accept an auxiliary retractor blade (not shown). The adjustment housing 906 is configured to accept an adjustment mechanism (not shown) that couples to the head 904 and is used to pivot the head 904 relative to the bar 902, thereby allowing the angle at which the auxiliary retractor enters the incision to be adjusted. The adjustment mechanism may include, for example, a threaded and/or ratcheting assembly for pivoting the head 904.

Figure 10:
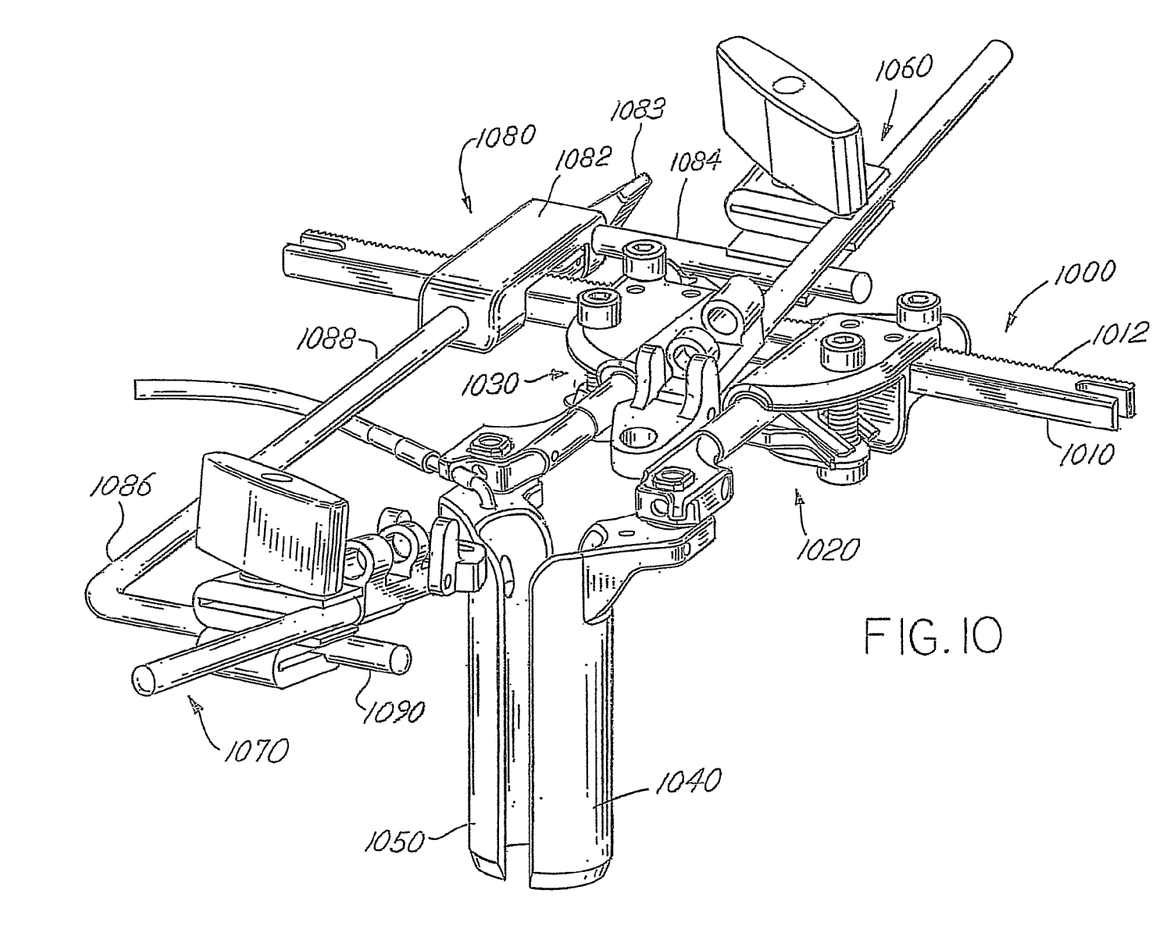
FIG. 10 illustrates a perspective view of a posterior lumbar retractor system formed in accordance with an embodiment of the present invention.

FIG. 10 illustrates a perspective view of a posterior lumbar retractor system 1000 formed in accordance with an embodiment of the present invention. The posterior lumbar retractor system 1000 may be similar in many respects to the posterior lumbar retractor system 600, but differs in certain respects. The posterior lumbar retractor system 1000 includes a spreader bar 1010, a first positioning assembly 1020, a second positioning assembly 1030, a first retractor 1040, a second retractor 1050, a first auxiliary retractor assembly 1060, a second auxiliary retractor system 1070, and a mounting assembly 1080.

The spreader bar 1010 is similar in many respects to the above described spreader bar 620. For example, the spreader bar 1010 may include teeth 1012 designed to cooperate with the positioning assemblies to allow the positioning assemblies to move along at least a portion of the length of the spreader bar 1010. The spreader bar 1010 differs from the spreader bar 620, for example, in that the spreader bar 1010 has a substantially constant width and height from end to end. This can help ease sliding the positioning assemblies on and off from either end.

The posterior lumbar retractor system 1000 includes a first auxiliary retractor assembly 1060 that is positioned and configured substantially similarly to the auxiliary retractor assembly of the posterior lumbar retractor system 600, and also includes a second auxiliary retractor assembly 1070. The second auxiliary retractor assembly 1070 in the illustrated embodiment comprises substantially similar components to the first auxiliary retractor assembly 1060. In certain embodiments, the auxiliary retractor assemblies may be configured differently from each other, and/or more than two auxiliary retractor assemblies may be used.

The mounting assembly 1080 of the embodiment illustrated in. FIG. 10 includes a body 1082, a securing assembly 1083, a first mounting bar 1084, and a second mounting bar 1086. The body 1082 is configured to fit around the spreader bar 1010, and also to accept and cooperate with the securing assembly 1083 to secure the body 1082 to the spreader bar 1010. For example, in the illustrated embodiment, the securing assembly 1083 includes a vise-like arrangement including a handle that is turned to rotate and advance a threaded member into the body 1082, thereby actuating a jaw like configuration that grasps the spreader bar 1010. As seen in FIG. 10, the mounting assembly 1080 is mounted off to the side of the positioning assemblies, in contrast to the mounting assembly of FIG. 9 which was interposed between the positioning assemblies.

The mounting assembly 1080 includes a first mounting bar 1084 and a second mounting bar 1086. The first mounting bar 1084 extends in a direction substantially parallel to the spreader bar 1010 when the mounting assembly 1080 is secured to the spreader bar 1010. In the illustrated embodiment, the first auxiliary retractor assembly 1060 is mounted to the first mounting bar 1084 with a clamp.

The second mounting bar 1086 includes a first portion 1088 and a second portion 1090. The first portion 1088 extends in a direction substantially perpendicular to the spreader bar 1010 when the mounting assembly 1080 is secured to the spreader bar 1010. The second portion 1090 extends in a direction substantially perpendicular to the first portion 1088 such that the second portion 1090 is substantially parallel to the first mounting bar 1084, but offset to the opposite side of the retractors 1040, 1050 as the first mounting bar 1084. Thus, in the illustrated embodiments, the second mounting bar 1086 provides a location to mount the second auxiliary retractor assembly 1070 such that it can hold a retractor that opposes a retractor held by the first auxiliary retractor assembly 1060. Further, in the illustrated embodiment, the auxiliary retractor assemblies and mounting bars are configured so that the auxiliary retractors (not shown) define an axis substantially perpendicular to an axis defined by the retractors 1040, 1050.

To use certain embodiments of retractor systems generally similar to the embodiments illustrated in FIGS. 9-10, an incision is first made to allow access to a site of interest. The positioning assemblies, with the retractors secured to the positioning assemblies proximate to the proximal end of the retractors, are positioned on the spreader bar such that the retractors associated with the positioning assemblies can be fit within the incision, and are generally laterally opposed and generally parallel to each other. Optionally, an instrument such as a dilator may be used to enlarge the incision and the retractors slid over the dilator. With the retractor blades in place, the spreader bar is secured in place to an external frame. Next, the lateral and angular position of the retractor blades may be adjusted independently as desired to provide access to the site of interest. For example, the retractors can be adjusted to be spread farther apart from each other laterally, and to adjust the angle at which the distal end extends into the incision. For example, by angling the distal ends so that one and/or the other is angled away from the opposing retractor, the site of interest may be enlarged near the proximal end of the retractor while not expanding, or helping reduce the expansion of, the incision at the exterior surface of the patient.

Because the blades can be adjusted independently, the provided volume of access to the site of interest does not need to be symmetric about the original insertion. Instead, the site may be laterally larger to one side compared to the other, and/or the retractors may extend at different angles inside the incision. This provides for improved flexibility in forming the access to a site of interest for different sizes of patients and/or procedures, and/or providing improved flexibility in selecting the incision location relative to the site of interest. In certain embodiments, the distal ends of the retractor blades may be fixed in place to the patient's anatomy. This may occur, for example, after the final position of the retractors is obtained. Further, in certain embodiments, one or more auxiliary retractors may be positioned to further assist in retracting tissue from and/or shaping the access to the site of interest.

While particular embodiments of the invention have been shown, it will be understood that the invention is not limited thereto since modifications may be made by those skilled in the art, particularly in light of the foregoing teaching. It is therefore, the appended claims that define the true spirit and scope of the invention.

What is claimed is:

1. A retractor system comprising:
a spreader bar;
a first positioning assembly adapted to secure a first retractor blade, the first positioning assembly including a first lateral positioning assembly configured to facilitate movement of the first positioning assembly laterally along at least a first portion of a length of the spreader bar, the first positioning assembly further including a first angular positioning assembly configured to facilitate angular adjustment of the first retractor blade relative to the spreader bar;
a second positioning assembly adapted to secure a second retractor blade, the second positioning assembly including a second lateral positioning assembly to facilitate movement of the second positioning assembly laterally along at least a second portion of the length of the spreader bar, the second positioning assembly further including a second angular positioning assembly configured to facilitate angular adjustment of the second retractor blade relative to the spreader bar;
wherein the first and second positioning assemblies are configured to facilitate independent angular and lateral movement of the first and second retractor blades with respect to each other; and
wherein said first and second angular positioning assemblies include a rotatable threaded post and a moveable arm engageably mounted to said threaded post for conjoint movement therewith, wherein rotation of said threaded post adjusts the angular position of the respective retractor blade.

2. The retractor system of claim 1 wherein the first lateral positioning assembly and the first angular positioning assembly are operable independent of one another so that the angle and lateral position of the first retractor blade are independently adjustable.

3. The retractor system of claim 1 wherein the spreader bar includes teeth that form a rack, and wherein the first and second lateral positioning assemblies each include a pinion that cooperates with the rack to facilitate lateral movement of the first and second positioning assemblies with respect to each other.

4. The retractor system of claim 1 wherein the first and second positioning assemblies each include a body and an arm, wherein the body accepts the arm, and wherein the arm is configured to accept a portion of the retractor blade associated with the positioning assembly.

5. The retractor system of claim 1 wherein the first and second angular positioning assemblies are configured to adjust a distal end of the retractor blade associated with the angular positioning assembly to be spaced farther from the other of the retractor blades than a proximal end of the retractor blade associated with the angular positioning assembly.

6. The retractor system of claim 5 wherein the first and second angular positioning assemblies are configured to adjust the proximal end of the retractor blade associated with the angular positioning assembly to be spaced farther from the other of the retractor blades than the distal end of the retractor blade associated with the angular positioning assembly.

7. The retractor system of claim 1 and further including a tool; and wherein the first lateral positioning assembly, first angular positioning assembly, second lateral positioning assembly, and second angular positioning assembly are configured to be independently adjustable by said tool.

8. The retractor system of claim 1 wherein the spreader bar has a substantially constant width and height from end to end.

9. A retractor system comprising:
   a frame including a crossbar;
   first and second arms each extending in a direction crosswise to the crossbar, each of the first and second arms having a proximal portion, a distal portion, and a rotation axis extending along a longitudinal portion of the arm in the direction crosswise to the crossbar;
   first and second retractor blades each having a distal portion and a proximal portion, wherein the proximal portion of the first retractor blade is configured for securement proximate the distal portion of the first arm and extends in a direction transverse to the first arm, wherein the proximal portion of the second retractor blade is configured for securement proximate the distal portion of the second arm and extends in a direction transverse to the second arm;
   a first positioning unit configured to allow adjustment of the first arm and first blade laterally along the crossbar and rotation of the first arm about its rotation axis; and
   a second positioning unit configured to allow adjustment of the second atm and second blade laterally along the crossbar and rotation of the second arm about its rotation axis, wherein each of the first and second positioning units includes,
      a crossbar locking mechanism configured to engage the crossbar, wherein the crossbar locking mechanism secures the positioning unit to the crossbar when in a locked state and allows lateral movement of the respective positioning unit laterally along the crossbar when in an unlocked state,
      an arm locking mechanism configured to engage the proximal portion of a respective arm and to secure the proximal portion of the respective arm with the crossbar locking mechanism of the positioning unit, wherein the arm locking mechanism secures the proximal portion of the respective arm to prevent rotation of the respective arm about its rotation axis when in a locked state, and wherein the respective arm locking mechanism releases the proximal portion of the respective arm to allow rotation of the respective arm about its rotation axis when in an unlocked state, wherein rotation of the respective arm about its rotation axis results in a corresponding angular movement of the respective retractor blade; and wherein the respective arm locking mechanism includes:
         (i) A rotatable threaded post; and
         (ii) an engagement arm mounted relative to and in engagement with said threaded post for causing angular movement of said engagement arm as said threaded post rotates,
      whereby a smooth angular movement of the respective retractor blade is provided.

10. The retractor system of claim 9, wherein the crossbar locking mechanism of a respective positioning unit and the arm locking mechanism of the respective positioning unit are fixed with one another.

11. The retractor system of claim 9, wherein the arm locking mechanism of the first positioning unit controls rotation of the first arm about its rotation axis and angular movement of the first blade, and the arm locking mechanism of the second positioning unit controls rotation of the second arm about its rotation axis and angular movement of the second blade, wherein rotation of the first arm and corresponding angular movement of the first blade are independent of the rotation of the second arm about its rotation axis and corresponding angular movement of the second blade.

12. The retractor system of claim 9, wherein the distal portions of the first and second retractor blades are securable to a portion of a patient's anatomy during a surgical procedure, and rotational movement of a respective arm about its respective rotation axis results in movement of the proximal portion of the respective retractor blade while the distal portion of the respective retractor blade remains secured proximal to an operative site.

13. The retractor system of claim 9 wherein the crossbar is a spreader bar including teeth to form a rack, and the crossbar locking mechanisms each include a pinion that cooperates with the rack to facilitate lateral movement of the respective positioning unit laterally along the crossbar.

14. A retractor system comprising:
   a frame including a crossbar;
   a first arm disposed at a lateral location along the crossbar, the first arm having a proximal portion and a distal portion;
   a second arm extending in a direction crosswise to the crossbar, the second arm having a proximal portion, a distal portion, and a rotation axis extending along a longitudinal portion of the second arm in a direction crosswise to the crossbar;
   first and second retractor blades each having a distal portion and a proximal portion, wherein the proximal portion of the first retractor blade is configured for securement proximate the distal portion of the first arm and extends in a direction transverse to the first arm, wherein the proximal portion of the second retractor blade is configured for securement proximate the distal portion of the second arm and extends in a direction transverse to the second arm; and
   a positioning unit associated with the second arm and second blade, wherein the positioning unit includes,
      a crossbar locking mechanism configured to engage the crossbar, wherein the crossbar locking mechanism secures the positioning unit to the crossbar when in a locked state and allows lateral movement of the positioning unit along the crossbar when in an unlocked state,
      an arm locking mechanism fixed with the crossbar locking mechanism and configured to engage the proximal portion of the second arm, wherein the arm locking mechanism secures the proximal portion of the respective arm to prevent rotation of the second arm about its rotation axis when in a locked state, wherein the arm locking mechanism releases the proximal portion of the second arm to allow rotation of the second arm about its rotation axis when in an unlocked state, wherein rotation of the second arm about its rotation axis results in a corresponding angular movement of the second retractor blade; and wherein the arm locking mechanism includes:
  (i) a rotatable threaded post; and
  (ii) an engagement arm secured to the second arm, said engagement arm being mounted relative to and in engagement with said threaded post for causing angular movement of said engagement arm as said threaded post rotates so as to cause rotation of the second arm about its rotation axis resulting in a smooth corresponding angular movement of the second retractor blade.

15. The retractor system of claim 14, wherein the distal portions of the first and second retractor blades are securable to a portion of a patient's anatomy during a surgical procedure, and rotational of the second arm about its rotation axis results in pivoting of the proximal portion of the second retractor blade while the distal portion of the second retractor blade remains secured proximal to an operative site.

16. The retractor system of claim 14, wherein the crossbar is a spreader bar including teeth to form a rack, and the crossbar locking mechanism includes a pinion that cooperates with the rack to facilitate lateral movement of the positioning unit laterally along the crossbar.

* * * * *